US009555020B2

(12) United States Patent
Pasricha et al.

(10) Patent No.: US 9,555,020 B2
(45) Date of Patent: Jan. 31, 2017

(54) TREATMENTS FOR DIABETES MELLITUS AND OBESITY

(75) Inventors: Pankaj Jay Pasricha, Columbia, MD (US); Liansheng Liu, Cockeysville, MD (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 43 days.

(21) Appl. No.: 14/233,732

(22) PCT Filed: Jul. 18, 2012

(86) PCT No.: PCT/US2012/047134
§ 371 (c)(1),
(2), (4) Date: Mar. 4, 2014

(87) PCT Pub. No.: WO2013/012892
PCT Pub. Date: Jan. 24, 2013

(65) Prior Publication Data
US 2014/0187619 A1  Jul. 3, 2014

Related U.S. Application Data

(60) Provisional application No. 61/509,491, filed on Jul. 19, 2011, provisional application No. 61/637,444, filed on Apr. 24, 2012.

(51) Int. Cl.
A61K 31/36    (2006.01)
A61N 7/00     (2006.01)
A61B 18/02    (2006.01)
A61B 18/04    (2006.01)
A61B 18/18    (2006.01)
(Continued)

(52) U.S. Cl.
CPC ............... *A61K 31/36* (2013.01); *A61B 18/02* (2013.01); *A61B 18/04* (2013.01); *A61B 18/12* (2013.01); *A61B 18/18* (2013.01); *A61B 18/1815* (2013.01); *A61B 18/20* (2013.01); *A61K 31/165* (2013.01); *A61K 31/357* (2013.01);
(Continued)

(58) Field of Classification Search
CPC .... A61K 31/36; A61K 31/165; A61K 31/357; A61B 18/04; A61N 7/00
See application file for complete search history.

(56) References Cited

U.S. PATENT DOCUMENTS 7,326,207 B2   2/2008   Edwards
7,544,365 B2   6/2009   Dosch et al.
(Continued)

OTHER PUBLICATIONS

Holle et al (Am J Physiol. Apr. 1990;258(4 Pt 1):G519-26).*
(Continued)

*Primary Examiner* — Savitha Rao
*Assistant Examiner* — Angela Brown-Pettigrew
(74) *Attorney, Agent, or Firm* — Davis, Brown, Koehn, Shors & Roberts, P.C.; Sean D. Solberg

(57) ABSTRACT

Methods of treatment in subjects suffering from diabetes mellitus or obesity are provided. The methods comprise the step of administering an active agent directly to the small intestine in the subject. In particular, the active agent may be administered directly to the duodenum in the subject. The active agents useful in the treatments described herein include analgesic agents and, in particular, antinociceptive agents such as capsaicin, resiniferatoxin, and their analogs.

15 Claims, 2 Drawing Sheets

(51) Int. Cl.
  *A61B 18/20* (2006.01)
  *A61K 31/165* (2006.01)
  *A61K 31/357* (2006.01)
  *A61B 18/12* (2006.01)
  *A61B 18/00* (2006.01)

(52) U.S. Cl.
  CPC ...... *A61N 7/00* (2013.01); *A61B 2018/00434* (2013.01); *A61B 2018/00494* (2013.01)

(56) References Cited

U.S. PATENT DOCUMENTS

| | | | |
|---|---|---|---|
| 8,367,733 B2 | 2/2013 | Burch et al. | |
| 8,455,504 B2 | 6/2013 | Gram et al. | |
| 2004/0089313 A1 | 5/2004 | Utley et al. | |
| 2008/0275445 A1* | 11/2008 | Kelly | A61B 18/1492 606/45 |
| 2009/0012154 A1* | 1/2009 | Pasricha | A61K 31/551 514/450 |
| 2009/0312255 A1 | 12/2009 | Dosch et al. | |

OTHER PUBLICATIONS

Moesgaard et al (Am J Physiol Endocrinol Metab 288: E1137—E1145, 2005).*
Premkumar et al (Current Neuropharmacology, 2008, 6, 151-163).*
Akiba et al (Am. J. Physiol. 277 (Gastrointest. Liver Physiol. 40): G268—G274, 1999).*
Razavi et al. (2006) TRPV1+ sensory neurons control beta cell stress and islet inflammation in autoimmune diabetes. Cell 127:1123-1135.
Gram et al. (2005) Sensory nerve desensitization by resiniferatoxin improves glucose tolerance and increases insulin secretion in Zucker Diabetic Fatty rats and is associated with reduced plasma activity of dipeptidyl peptidase IV. Eur. J. Pharmacol. 509(2-3):211-217.
Flatt (2007) Effective surgical treatment of obesity may be mediated by ablation of the lipogenic gut hormone gastric inhibitory polypeptide (GIP): evidence and clinical opportunity for development of new obesity-diabetes drugs? Diab. Vasc. Dis. Res. 4(2):151-153.
Kang et al. (2010) Dietary capsaicin reduces obesity-induced insulin resistance and hepatic steatosis in obese mice fed a high-fat diet. Obesity (Silver Spring) 18(4):780-787.

* cited by examiner

TREATMENTS FOR DIABETES MELLITUS AND OBESITY

CROSS-REFERENCE TO RELATED APPLICATIONS

This application is a national phase application of PCT International Application No. PCT/US2012/047134, filed Jul. 18, 2012, which claims the benefit of U.S. Provisional Application No. 61/509,491, filed on Jul. 19, 2011, and U.S. Provisional Application No. 61/637,444, filed on Apr. 24, 2012, the disclosures each of which are incorporated herein by reference in their entireties.

BACKGROUND OF THE INVENTION

Diabetes mellitus, or simply diabetes, is a metabolic condition, or combination of conditions, in which an individual displays high concentrations of blood glucose. The condition is caused either by insufficient production of insulin within the body or by the failure of cells to respond properly to the insulin that is produced.

Diabetes is one of the leading causes of death and disability in the United States and in other developed countries. Diabetes is associated with long-term complications affecting almost every part of the body. For example, the disease can lead to blindness, heart and blood vessel disease, stroke, kidney failure, amputations, and nerve damage. Diabetes affects approximately 8 percent of the United States population, and the total cost of diabetes in the United States alone is estimated to approach $200 billion.

Diabetes is most typically classified as either type 1 diabetes (also referred to as insulin-dependent diabetes or juvenile diabetes), wherein the subject fails to produce sufficient insulin, type 2 diabetes (also referred to as non-insulin-dependent diabetes, adult-onset diabetes, or obesity-related diabetes), wherein the subject fails to respond properly to insulin, or gestational diabetes, wherein the condition develops in women late in pregnancy.

Type 1 diabetes results from the loss of insulin-producing beta cells in the pancreas, generally due to an autoimmune response against the beta cells. The cause of the autoimmune response is not known, but it is believed that genetic and environmental factors, including the possible involvement of viruses, could be involved. Symptoms of type 1 diabetes include increased thirst and urination, hunger, weight loss, blurred vision, and extreme fatigue. Although it can appear at any age, type 1 diabetes most frequently develops in children and young adults. Roughly 5 to 10 percent of all diabetes cases are considered type 1 diabetes.

Type 2 diabetes is the most common form of diabetes, accounting for 90 to 95 percent of all cases of diabetes. Type 2 diabetes is generally associated with older age, obesity, family history, previous history with gestational diabetes, and physical inactivity. It is also more prevalent in certain ethnicities. Type 2 diabetes is also referred to as insulin-resistant diabetes because the pancreas is usually able to produce sufficient amounts of insulin, but the body fails to respond properly to that insulin. As with type 1 diabetes, blood glucose levels in individuals suffering from type 2 diabetes increase, and the body is unable to metabolize the blood glucose efficiently. The symptoms of type 2 diabetes generally develop more slowly than those of type 1 diabetes. The symptoms include fatigue, frequent urination, increased thirst and hunger, weight loss, blurred vision, and slow healing of wounds or sores. In some cases, no symptoms are evident.

Gestational diabetes occurs in approximately 3 to 8 percent of pregnant women in the United States, generally developing late in the pregnancy. The disease typically disappears after birth of the baby, but women who have experienced gestational diabetes are significantly more likely to develop type 2 diabetes within 5 to 10 years than those who have not. Women who maintain reasonable body weight and are physically active after suffering from gestational diabetes may be less likely to develop type 2 diabetes than those who do not. As with type 2 diabetes, gestational diabetes occurs more frequently among women with a family history of diabetes and also in certain ethnic groups.

Since the discovery of insulin over 80 years ago, diabetes, particularly type 1, or insulin-dependent diabetes, has been a somewhat treatable condition. The combination of a proper diet, physical activity, and insulin injection, together with the monitoring of blood glucose levels using portable meters, allows the management of type 1 diabetes. For type 2 diabetics, healthy eating, physical activity, and monitoring blood glucose levels are also important. In some cases, drug therapies can be used to control blood glucose levels in these patients.

Other approaches to the treatment of diabetes are also desirable. For example, it has been shown that bariatric surgery for the treatment of gross obesity may also cure obesity-related diabetes. It is thought that this surgery, which involves bypass of at least a portion of the small intestine, could cause the surgical ablation of gastric inhibitory polypeptide (GIP)-secreting intestinal K cells. Flatt (2007) *Diab. Vasc. Dis. Res.* 4, 150. As a result, circulating levels of GIP, which is thought to play a key role in lipid metabolism and fat deposition, are decreased.

Furthermore, although the underlying cause of type 1 diabetes remains unknown, a defect in a subset of sensory neurons that innervate the pancreas may play a role in initiating a series of events leading to local inflammation, destruction of islet cells in the pancreas, and autoimmune (type 1) diabetes. Razavi et al. (2006) *Cell* 127, 1123. In individuals with the defect, insulin secretion by beta cells fails to properly stimulate sensory neurons expressing a hypofunctional, polymorphic capsaicin receptor (TRPV-1=transient receptor potential vanilloid-1) to release neuropeptides. Suboptimal local levels of neuropeptides lead to insulin resistance and beta cell stress and ultimately an autoimmune response against the beta cells. Identifying methods to control these pathways could thus provide novel approaches for treating or preventing diabetes.

Another health problem of major importance, particularly in the developed world, is obesity. Obesity is a complex, multifactorial and chronic condition characterized by excess body fat. Obesity results from an imbalance between energy expenditure and caloric intake. Although the causes of this imbalance are not completely understood, genetic and/or acquired physiologic events and environmental factors are important. The adverse health effects of obesity, and more particularly morbid obesity, have become well-known in recent years. Such adverse health effects include, but are not limited to, cardiovascular disease, diabetes, high blood pressure, arthritis, and sleep apnea. Generally, as a patient's body mass index (BMI) rises, the likelihood of suffering the adverse health effects of obesity also rises.

Often, surgery has been the only therapy that ensures real results in patients who have BMI values close to, or in excess of, 40 kg/m². Modern surgical procedures generally entail either (1) the reduction of gastric compliance, with the aim of limiting the subject's ability to ingest food, or (2) the reduction of the food absorption surface by shortening or bypassing part of the digestive canal. In some cases, both aims are sought through the same surgical procedure. The risk and invasiveness factors of currently available surgeries are often too great for a patient to accept to undergo surgical treatment for treatment of obesity. Accordingly, there is a need for less invasive, yet effective treatment procedures for the morbidly obese. Also, since the current surgical procedures are currently indicated only for those patients having a BMI of 40 or greater, or 35 or greater, when co-morbidities are present, it would be desirable to provide a less invasive procedure that would be available for slightly less obese patients, e.g., patients having a BMI of 30 to 35 who are not indicated for the currently available surgical procedures.

U.S. Patent Application Publication No. 2008/0275445 reports devices for use in ablating tissue in the wall of luminal organs of the gastrointestinal tract. See also U.S. Pat. No. 7,326,207. Such devices are purportedly useful in the treatment of pathophysiological metabolic conditions, such as type 2 diabetes, insulin resistance, obesity, and metabolic syndrome, but the effectiveness of such treatments has not been demonstrated.

U.S. Patent Application Publication No. 2004/0089313 reports systems and methods for treating obesity and other gastrointestinal conditions by targeting the stomach. In particular, the methods purportedly cause tightening of the pyloric sphincter or alteration of the receptive relaxation of stomach muscles. The treatments include ablation of stomach tissue and, in some cases, injection of a cytokine or a vanilloid-containing compound into stomach tissue. The effectiveness of these treatments has not, however, been reported.

Given the widespread and growing significance of diabetes and obesity throughout the population, there is clearly a strong need for additional methods of treating and preventing these diseases.

SUMMARY OF THE INVENTION

The instant disclosure addresses these and other problems by providing in one aspect methods of treatment comprising ablation of a region of the small intestine in a subject, wherein the subject suffers from diabetes mellitus or obesity.

In preferred embodiments, the region of the small intestine is a region of the duodenum.

In some embodiments, the ablation targets a sensory nerve.

In some embodiments of the invention, the ablation is a mechanical, electrical, thermal, radiative, or chemical ablation. In specific embodiments, the ablation is a laser, ultrasound, radiofrequency, alternating current, microwave, or thermal ablation. In preferred embodiments, the ablation is a radiofrequency or alternating current ablation. In highly preferred embodiments, the ablation is a pulsed radiofrequency ablation.

In other highly preferred embodiments of the invention, the ablation is a chemical ablation. According to some of these embodiments, the chemical ablation may comprise administering an active agent directly to the small intestine in a subject, wherein the subject suffers from diabetes mellitus or obesity.

In preferred embodiments, the active agent is administered directly to the duodenum.

In some embodiments, the active agent causes ablation of sensory nerves.

According to some specific embodiments of the invention, the subject suffers from diabetes mellitus. In more specific embodiments, the subject suffers from type 2 diabetes mellitus.

According to other specific embodiments of the invention, the subject suffers from obesity.

In preferred embodiments of the invention, the active agent administered in the chemical ablation is an analgesic agent. In specific embodiments, the analgesic agent is an antinociceptive agent. In more specific embodiments, the antinociceptive agent is selected from the group consisting of capsaicin, a capsaicin analogue, resiniferatoxin, and a resiniferatoxin analogue.

According to some specific embodiments, the antinociceptive agent of the disclosed methods is capsaicin or a capsaicin analogue. In other specific embodiments, the antinociceptive agent is resiniferatoxin or a resiniferatoxin analogue. In specific preferred embodiments, the antinociceptive agent is resiniferatoxin.

In some embodiments, the active agent used according to the methods of the invention is a ligand of the transient receptor potential cation channel subfamily V, member 1, receptor.

In preferred embodiments, the active agent is administered by injection. In other preferred embodiments, the active agent is administered by topical application.

According to some embodiments of the invention, the active agent is administered by infusion through a syringe.

In specific embodiments, the active agent of the disclosed methods is administered following surgical exposure of the small intestine of the subject. In other specific embodiments, the active agent is administered by a laparoscope or an endoscope.

In some specific preferred embodiments, the active agent of the disclosed methods is administered by topical application directly to the duodenum, wherein the active agent is resiniferatoxin or a resiniferatoxin analogue, and wherein the patient suffers from diabetes mellitus. In other specific preferred embodiments, the active agent is administered by topical application directly to the duodenum, wherein the active agent is resiniferatoxin or a resiniferatoxin analogue, and wherein the patient suffers from obesity.

In some preferred embodiments, the methods of the invention further comprise measuring oral glucose tolerance of the subject.

In other preferred embodiments, the methods further comprise measuring body weight change in the subject.

DETAILED DESCRIPTION OF THE INVENTION

Figure 1:
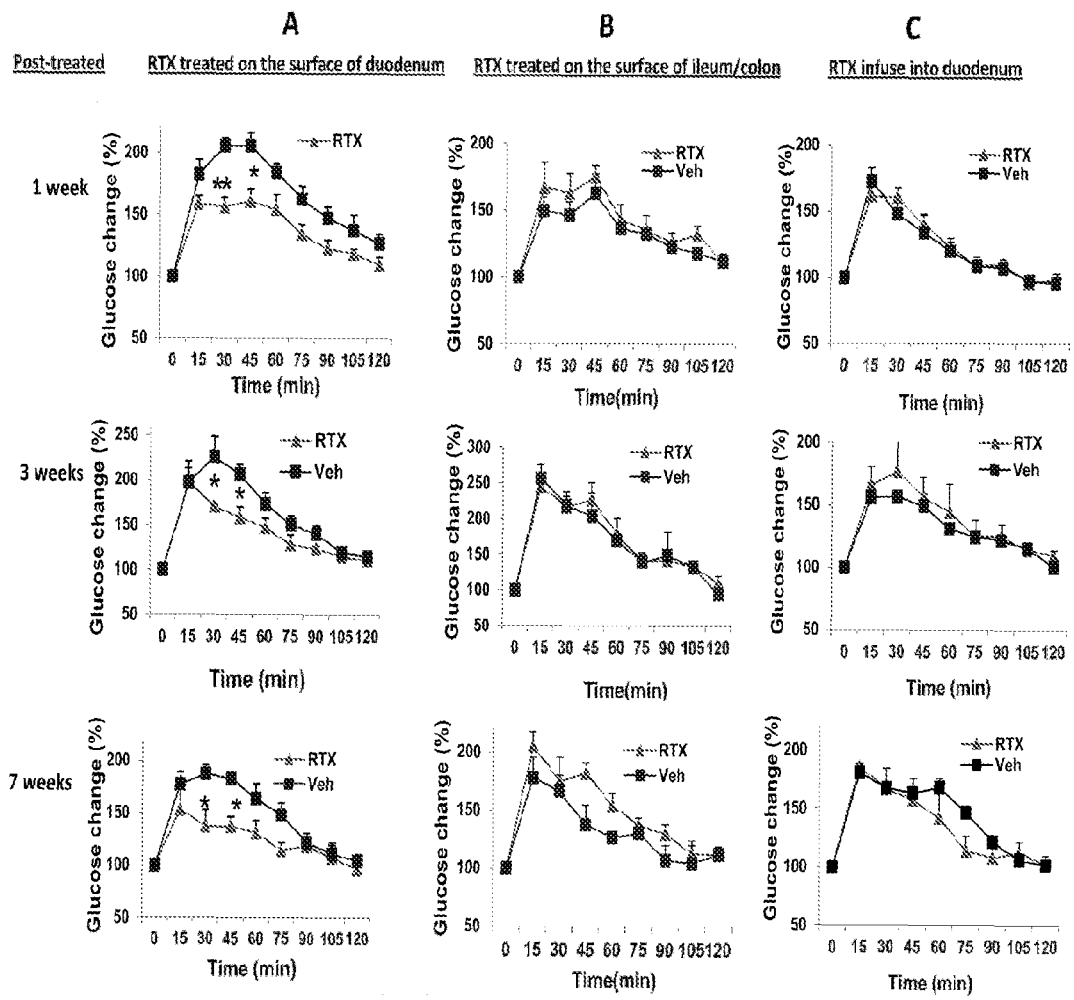
FIG. 1. Effect of RTX treatment on glucose tolerance in rats. (A) Treatment on the surface of the duodenum; (B) Treatment on the surface of the ileum/colon; and (C) Infusion into the duodenum.

The present disclosure provides novel treatment methods for subjects suffering from diabetes mellitus or obesity. Specifically, the methods disclosed herein comprise ablation of a region of the small intestine, preferably of the duodenum, and preferably wherein the ablation targets a sensory nerve, in the subject.

As used herein, the duodenum is a specific segment of the gastrointestinal tract (GI tract). In certain instances the term GI tract may refer to the "gut" or the "alimentary canal" that is a continuous, coiled, hollow, muscular tube that winds through the ventral body cavity. It is open to the external environment at both ends. In a human, its organs (gastrointestinal organs) generally include the mouth, pharynx, esophagus, stomach, small intestine (duodenum, jejunum, and ileum), and large intestine (cecum, appendix, colon, rectum, and anal canal). The large intestine leads to the terminal opening, or anus.

The small intestine is the longest section of the digestive tract and is divided into three segments: the duodenum, jejunum and ileum, each of which performs different digestive functions. When the stomach contents move to the duodenum, the first segment of the small intestine, bile and pancreatic juice speed up digestion. Most of the iron and calcium in the food we eat is absorbed in the duodenum. The jejunum and ileum, the remaining two segments of the nearly 20 feet of small intestine, complete the absorption of almost all calories and nutrients. The food particles that cannot be digested in the small intestine are stored in the large intestine until eliminated.

Bariatric surgery produces weight loss by restricting food intake and, in some cases, by interfering with nutrition through malabsorption. In particular, bariatric surgeries in which all or part of the duodenum is bypassed are believed to cause a decrease in the absorption of food and thus result in weight loss in the patient. Furthermore, patients undergoing gastric bypass surgery in which the duodenum is bypassed are frequently cured of their type 2 diabetes. Pories et al. 1995, *Ann. Surg.* 222, 339. The exact physiological bases for these effects remain unknown, although studies in a non-obese diabetic rat model demonstrate that bypass surgery improves glycemic control with a significant decrease in leptin and glucagon levels after oral glucose overload. Pacheco et al. 2007 *Am. J. Surg.* 194, 221. The effects of bypass surgery on diabetes do not, therefore, result simply from surgically induced weight loss or decreased caloric intake. More recent randomized clinical trials have demonstrated that gastric bypass surgery in obese patients, either in combination with intensive medical therapy or not, results in the remission of type 2 diabetes in a significant number of those patients. Schauer et al. 2012 Mar. 26 *N. Engl. J. Med.* (epublication); Mingrone et al. 2012 Mar. 26 *N. Engl. J. Med.* (epublication). Bariatric surgery is an extreme procedure, however, that is not typically indicated for non-obese diabetic patients. Alternative less costly and less invasive approaches to the treatment of diabetic and obese patients are therefore desirable.

As described herein, the methods of the instant disclosure comprise ablation of a region of the small intestine in a subject suffering from diabetes mellitus or obesity. The methods of the instant disclosure are significantly less invasive than, for example, bariatric surgery, and will therefore result in lower morbidity and mortality in the treated subjects. The instant methods are also faster and less complicated than alternative methods of treatment and will therefore result in cost savings compared to those methods.

In preferred embodiments of the instant invention, the ablation targets a sensory nerve of the small intestine, or more particularly, of the duodenum. Without intending to be bound by theory, it is believed that such sensory nerves may be involved in the loss of glycemic control in diabetic and obese patients and may therefore serve as desirable targets for ablation according to the methods of the instant invention. Of particular interest in the practice of the methods of the instant invention is the targeting of sensory nerves that express the transient receptor potential cation channel subfamily V, member 1 (TRPV-1) receptor. Such targeting can be accomplished, for example, by immunolabeling or other labeling techniques during the ablation procedure, as would be understood by those of ordinary skill in the art. In some embodiments of the invention, however, sensory nerves of the small intestine or duodenum are targeted more generally in the abalation step, or they may not be targeted at all. In preferred embodiments of the invention, the targeted sensory nerve is on the serosal surface of the small intestine, most preferably on the serosal surface of the duodenum Ablation of a region of the small intestine may be achieved according to the instant methods using, for example, mechanical, electrical, thermal, radiative, or chemical ablation. In particular, laser, ultrasound, radiofrequency, alternating current, microwave, or thermal ablation may be usefully employed in the practice of the instant methods.

In preferred embodiments, radiofrequency (RF) fields, such as, for example, pulsed radiofrequency fields, may be usefully employed in the ablation. Such pulsed radiofrequency fields are effective in reducing pain and other neuropathic syndromes, possibly by causing ultrastructural changes in the neural structures to which they are applied. The techniques appear to selectively target C-fibers and A-delta fibers, the principal sensory nociceptor axons, compared to A-beta fibers, which are related to touch and non-pain-related sensations. See, e.g., Erdine et al. 2009 *Pain Pract.* 9 407-417. Pulsed RF techniques generate less heat in the target tissues than continuous RF techniques and may therefore operate by different mechanisms. The amount of energy imparted by the RF device can be controlled and directed, as would be known and understood in the art, in order to achieve the desired effects and to minimize side effects. Use of selective ablation techniques, such as pulsed RF techniques, maximizes the effectiveness of the treatments against diabetes and obesity while minimizing side effects, such as, for example, those affecting tactile sensory inputs.

Radiofrequency ablation devices are well known in the surgical arts, and in particular in the art of cardiac surgery. See, e.g., U.S. Pat. Nos. 4,945,912; 5,281,218; 5,348,554; and 5,423,808. Such devices can be readily delivered to the desired location using a catheter or other equivalent device. Radiofrequency ablation of the basivertebral nerve has recently been shown to reduce chronic back pain in clinical studies using devices designed to target intraosseous nerves. See, e.g., PCT International Publication No. WO 01/57655; U.S. Pat. No. 7,749,218. Analogous devices may be adapted for the practice of the methods of the instant invention.

In other preferred embodiments of the invention, ablation of a region of the small intestine may be achieved using other electrical techniques, such as, for example, high-frequency alternating current stimulation. Such treatments have been shown to reversibly block the conduction of an action potential through nerve cells. Variation in the frequency and amplitude of the stimulation provides selective effects on different nerve fibers and thus allows for more control over the outcome of the treatments, including the minimization of side effects. Specifically, the stimulation by high-frequency alternating current is selective in blocking slow-conducting, unmyelinated C-fibers, such as those of nociceptive neurons, while minimizing effects on fast-conducting myelinated A-fibers. See, e.g., Joseph et al. 2011 *IEEE Trans Neural Syst Rehabil Eng.* 19 550-557. Such selectivity is useful in the methods of the instant invention in targeting sensory neurons of the small intestine and duodenum and thus in improving glycemic control and weight loss.

In some embodiments of the invention, it may be preferable for the ablation to be reversible, whereas in other embodiments, it may be preferable for the ablation to be irreversible. Adjustment and optimization of the ablation technique to achieve the desired outcome, such as, for example, the recovery of glycemic control in a diabetic patient or the loss of weight in an obese patient, are within the skill of the ordinary artisan.

In some embodiments of the invention, the ablation of a region of the small intestine is achieved using a chemical ablation technique. In specific embodiments, the methods comprise administering an active agent directly to the small intestine in a subject. The active agent usefully administered according to these methods is selected for its effectiveness in treating diabetes mellitus and/or obesity upon direct administration. In particular, the active agent used in some of the disclosed methods may cause ablation of sensory nerves in the small intestine, and more specifically in the duodenum, and thus be effective in treating these conditions.

In some embodiments, the active agent used according to some of the instant methods may be an analgesic agent. Analgesic agents are widely used and well known in the medical arts. Such analgesic agents may, for example, be topical or systemic. Examples of topical analgesics are lidocaine and capsaicin. In some embodiments, the analgesic agent may be a psychotropic agent that has analgesic properties.

In preferred embodiments of the instant methods, the analgesic agent is an antinociceptive agent, specifically an agent that targets nociceptors on the surface of the small intestine, and in particular on the surface of the duodenum. In some embodiments of the instant methods, the antinociceptive agent is selected from the group consisting of capsaicin, a capsaicin analogue, resiniferatoxin, and a resiniferatoxin analogue.

Resiniferatoxin and capsaicin and their analogues are exogenous ligands for the transient receptor potential cation channel subfamily V, member 1 (TRPV-1), formerly known as the Vanilloid receptor 1 (VR1). The only known endogenous ligand for this receptor is the proton. TRPV-1 receptors are found on the visceral sensory nerve fibers of the unmyelinated type (C-fiber) and the thinly myelinated type (A-fiber). TRPV-1 functions as a modulator of sensory nerve responses to various noxious stimuli.

In some embodiments of the instant methods, the antinociceptive agent is capsaicin or a capsaicin analogue. Capsaicin is the main pungent component in hot pepper. Capsaicin treatment in animals can cause a variety of physiological effects. For example, systemic capsaicin treatment has been reported to alter serum glucose and free fatty acid concentrations in rats and also to modulate the effects of insulin on the levels of serum glucose and free fatty acids. At high levels, systemic capsaicin can cause the lesioning of afferent nerves in neonatal rats. Spiridonov et al. (2000) *Neurosci. Behav. Physiol.* 30, 207. Such desensitization of sensory nerves can improve glucose tolerance and insulin sensitivity in treated animals. Desensitization by capsaicin is also reported to delay the progression of type 2 diabetes in the Zucker fatty rat model. Gram et al. (2000) *Diabetes* 49, Suppl. 1, A428. It has further been reported that plasma levels of calcitonin gene-related peptide (CGRP) are elevated in these rats prior to the onset of obesity and that the increased activity of sensory nerves therefore precedes the development of obesity and insulin resistance in this model. Gram et al. (2005) *Eur. J. Endocrinol.* 153, 963.

Treatment of Zucker diabetic rats with systemic capsaicin reportedly targets the expression of TRPV-1 receptors in CGRP-expressing primary sensory fibers in pancreatic islets of Langerhans cells and prevents the deterioration of metabolism and glucose homeostasis in these animals. Gram et al. (2007) *Eur. J. Neurosci.* 25, 213. Furthermore, mutations in conserved regions of the TRPV-1 receptor have been identified in non-obese diabetic mice and have been correlated with neurogenic inflammation in islet beta cells. Razavi et al. (2006) *Cell* 127, 1123. Without intending to be bound by theory, TRPV-1 may therefore play a role in the development of both type 1 and type 2 diabetes through a combination of neuronal and autoimmune events. See also Bour-Jordan and Bluestone (2006) *Cell* 127, 1097; Tsui et al. (2007) *Trends Mol. Medicine.* 13, 405.

TRPV-1 is highly expressed in sensory neurons, but it has also been detected in mouse embryo 3T3-L1 preadipocytes and in human and mouse visceral adipose tissue. Zhang et al. (2007) *Circ. Res.* 100, 1063. Capsaicin is reported to induce calcium influx through the TRPV-1 receptor in a dose-dependent manner in the preadipocyte cells and to prevent adipogenesis in stimulated cells. Adipose tissue from obese humans reportedly displays decreased expression of the TRPV-1 receptor, and these cells likewise show a reduced capsaicin-induced calcium influx. Studies in TRPV-1 knock-out mice support a role for the receptor in adipogensis and obesity in vivo. Oral administration of capsaicin in mice was reported to prevent obesity in wild-type animals but not in TRPV-1 knockout mice fed a high-fat diet. Activators of TRPV-1 may therefore prevent adipogenesis and obesity.

In some preferred embodiments, the antinociceptive agent of the instant methods is resiniferatoxin or a resiniferatoxin analogue. Resiniferatoxin (RTX) is a naturally occurring super-analogue of capsaicin. It is found naturally in the latex of Euphorbia plants. Resiniferatoxin induces the desensitization effect and neuronal ablation more potently than capsaicin and with minimal initial activation of the TRPV-1 neuron. Resiniferatoxin, and a number of agonists based on the structures of capsaicin and resiniferatoxin have been reported as potential analgesics through desensitization/denervation of these neurons. RTX is reportedly less toxic than capsaicin when administered systemically.

Resiniferatoxin may be used to alleviate acute or chronic nausea, vomiting, or a combination thereof, by localized ablation of vagal afferent nerves in the stomach or other regions of the gastrointestinal tract. See U.S. Patent Application Publication No. 2009/0012154 A1, and references cited therein. It may also be used to ablate both pain responses and neurogenic inflammation. See U.S. Patent Application Publication No. 2010/0204313 A1, and references cited therein. Furthermore, subcutaneous injection of resiniferatoxin in early diabetic rats may prevent further deterioration of glucose homeostatis, and administration to overtly diabetic rats may improve glucose tolerance in those animals. Gram et al. (2005) *Eur. J. Pharm.* 509, 211. Such treatments are likewise reported to improve the sensitivity of the animals to insulin. Moesgaard et al. (2005) *Am. J. Physiol. Endocrinol. Metab.* 288 E1137.

RTX has been used to selectively ablate nociceptive neurons in the treatment of hyperalgesia and neurogenic inflammation. Tender et al. (2005) *J. Neurosurg.* 102, 522. The effects of RTX on pain and inflammation occur without significant effects on normal tactile sensation or motor function. The treatments target nociceptive neurons expressing the TRPV-1 receptor and, in particular, the so-called C-fiber and A-delta fiber neurons. Since the majority of nerve fibers in the duodenum are C-fiber and A-delta fiber neurons, one of the features of some embodiments of the instant invention is to selectively target sensory nerves of the small intestine and duodenum using capsaicin, RTX, and other ligands of the TRPV-1 receptor.

The chemical synthesis of resiniferatoxin has been reported. Wender et al. (1997) *J. Am. Chem. Soc.* 119, 12976.

Accordingly, in some embodiments of the instant methods, the active agent used in the methods is a ligand of the TRPV-1 receptor. As described above, examples of such ligands include capsaicin and RTX.

The instant disclosure therefore also provides in another aspect a ligand of the TRPV-1 receptor for use in treating diabetes mellitus or obesity. In preferred embodiments, the disclosure provides capsaicin, RTX, or the like, for use in treating diabetes mellitus or obesity.

In some embodiments of the instant methods, a single active agent may be administered directly to the small intestine, and more specifically, to the duodenum, in a subject. In some embodiments, combinations of active agents may be used in the methods of treatment disclosed herein.

As recited in some of the instant methods, an active agent may be administered directly to the small intestine in a subject. Direct administration of the active agent is in contrast to systemic administration, in which an active agent is, for example, injected into the bloodstream of a subject, is injected into the subject subcutaneously or intramuscularly, or is administered in any other way that does not significantly localize the effects of the active agent to the small intestine or duodenum. Direct administration may, for example, involve exposing the small intestine or duodenum directly to a stream of solution containing the active agent. In some embodiments, the active agent may be administered to the small intestine or duodenum by topical application. In some embodiments, tissues or organs adjacent to the small intestine or duodenum may be protected from exposure to the active agent, for example, by the placement of sponges or other physical barriers. In some embodiments, the active agent may be administered by a syringe. In some embodiments, the active agent may be administered by a cotton applicator, or other similar device. In some embodiments, the active agent may be administered by another corresponding method.

According to some preferred embodiments of the instant methods, an active agent may be administered directly to the serosal surface of the duodenum. As would be understood by those of ordinary skill in the art, the duodenum is comprised of layers, including the serosa, the muscularis, the submucosa, and the mucosa.

The active agent or agents of the instantly disclosed methods may be provided in any manner that is effective in the treatment of a subject suffering from diabetes mellitus or obesity. For example, the agent may be dissolved in a solution for direct administration to the small intestine, and, in preferred embodiments, to the duodenum. The solution may contain other agents to, for example, stabilize or improve solubility of the active agent. The solution may be an aqueous solution or another solution capable of delivering the active agent to the subject in an effective form. In some embodiments, as would be understood by the skilled artisan, the solution may be a mixture of solvents and may include other agents, such as, for example, detergents, such that the active agent is effectively delivered to the subject. In preferred embodiments, the active agent is dissolved in aqueous solution. In other preferred embodiments, the solution also contains an alcohol. In still other preferred embodiments, the solution also contains a detergent. In highly preferred embodiments, the solution contains both an alcohol and a detergent.

The active agent or agents of the instantly disclosed methods are provided at concentrations effective to treat a subject suffering from diabetes mellitus or obesity. For example, the active agent may be provided in a solution containing at least 1 ng, 3 ng, 10 ng, 30 ng, 100 ng, 300 ng, 1 µg, 3 µg, 10 µg, 30 µg, 100 µg, 300 µg, 1 mg, 3 mg, 10 mg, 30 mg, 100 mg, or even more active agent per mL solution. The active agent may be provided in a solution containing at most 100 mg, 30 mg, 10 mg, 3 mg, 1 mg, 300 µg, 100 µg, 30 µg, 10 µg, 3 µg, 1 µg, 300 ng, 100 ng, 30 ng, 10 ng, 3 ng, 1 ng, or even less active agent per mL solution. In preferred embodiments, the solution contains the active agent from about 100 ng/mL to about 10 mg/mL solution. In more preferred embodiments, the solution contains the active agent from about 10 µg/mL to about 1 mg/mL solution. In even more preferred embodiments, the solution contains the active agent at about 200 µg/mL.

Administration of active agents according to some methods of the instant disclosure may, in some embodiments, be accomplished by surgical techniques. For example, the active agent may in some embodiments be administered following surgical exposure of the small intestine of the subject. Surgical exposure of the small intestine may be accomplished by any appropriate means, as would be understood by those of skill in the art.

Administration of active agents according to some methods of the instant disclosure may, in some embodiments, not necessarily require the surgical exposure of the small intestine of the subject. For example, the active agent may be administered in some embodiments by endoscopic or laparoscopic surgical techniques. Endoscopic or laparoscopic administration may be accomplished by either using the endoscope or laparoscope for both visualization as well as administration of the agent or by endoscopic or laparoscopic visualization to guide administration of the agent.

General endoscopic procedural techniques such as visualizing, dilating, cutting, and manipulating tissue, and administering active agents, may be accomplished using flexible devices such as endoscopes, balloons, snares and electrosurgical tools well known in the art. Laparoscopy or visualization of the peritoneal cavity may be done, for example, with a flexible scope, as is typically used for diagnostic purposes, or with a rigid scope, as is typically used for therapeutic procedures. With the rigid scope procedures, a procedure is typically performed while being observed by secondary scopes positioned at various strategic positions in the peritoneal cavity. In some embodiments, flexible scopes that allow for visualization are not used for conducting the therapeutic procedures by themselves, and the rigid scopes that have the tools necessary to perform the tasks associated with the therapeutic procedures make use of additional flexible scopes so the doctor or operator can view the tasks and procedure being performed. In some embodiments, such as traditional gastrointestinal endoscopy, tasks may be performed with a scope that also allows the operator to view the tasks and procedures being performed. Gastrointestinal endoscopies may in some embodiments be limited to work within the lumen or interior tissue of the gastrointestinal tract or associated organs, and not in the peritoneal cavity. In other embodiments, the lumen of the gastrointestinal tract may, however, be breached by the endoscope in order to reach surfaces exposed to the peritoneal cavity. See, for example, U.S. Patent Application Publication No. 2007/0051380 A1. In some embodiments, injection into the desired layers may be enhanced using imaging guidance, such as by endoscopic ultrasound.

In some embodiments, the methods of the instant disclosure may further comprise the step of measuring oral glucose tolerance of the subject. Such measurement allows the efficacy of the treatment to be determined. Oral glucose tolerance may be measured by various methods, as would be understood by those skilled in the relevant art. For example, blood glucose may be measured in a subject using a standard glucose meter following the treatment methods. The blood glucose may be measured after fasting to establish a baseline blood glucose level in the subject. Oral glucose may then be provided to the subject, and blood glucose at subsequent times determined using the glucose meter to determine the oral glucose tolerance of the subject.

In some embodiments, the methods of the disclosure may further comprise the step of measuring body weight change in the subject. Such measurement may be helpful in determining the efficacy of treatment in subjects suffering from obesity and may, in some embodiments, be used in combination with the measurement of oral glucose tolerance in the subject.

Further Aspects

In yet other aspects, the invention provides novel methods of treatment according to the following numbered paragraphs:

1. A method of treatment comprising:
administering an active agent directly to the small intestine in a subject, wherein the subject suffers from diabetes mellitus or obesity.

2. The method of paragraph 1, wherein the active agent is administered directly to the duodenum.

3. The method of paragraph 1, wherein the active agent causes ablation of sensory nerves.

4. The method of paragraph 1, wherein the subject suffers from diabetes mellitus.

5. The method of paragraph 1, wherein the subject suffers from type 2 diabetes mellitus.

6. The method of paragraph 1, wherein the subject suffers from obesity.

7. The method of paragraph 1, wherein the active agent is an analgesic agent.

8. The method of paragraph 7, wherein the analgesic agent is an antinociceptive agent.

9. The method of paragraph 8, wherein the antinociceptive agent is selected from the group consisting of capsaicin, a capsaicin analogue, resiniferatoxin, and a resiniferatoxin analogue.

10. The method of paragraph 8, wherein the antinociceptive agent is capsaicin or a capsaicin analogue.

11. The method of paragraph 8, wherein the antinociceptive agent is resiniferatoxin or a resiniferatoxin analogue.

12. The method of paragraph 8, wherein the antinociceptive agent is resiniferatoxin.

13. The method of paragraph 1, wherein the active agent is a ligand of the transient receptor potential cation channel subfamily V, member 1, receptor.

14. The method of paragraph 1, wherein the active agent is administered by injection.

15. The method of paragraph 1, wherein the active agent is administered by topical application.

16. The method of paragraph 1, wherein the active agent is administered by infusion through a syringe.

17. The method of paragraph 1, wherein the active agent is administered following surgical exposure of the small intestine of the subject.

18. The method of paragraph 1, wherein the active agent is administered by a laparoscope or an endoscope.

19. The method of paragraph 1, wherein the active agent is administered by topical application directly to the duodenum, wherein the active agent is resiniferatoxin or a resiniferatoxin analogue, and wherein the patient suffers from diabetes mellitus.

20. The method of paragraph 1, wherein the active agent is administered by topical application directly to the duodenum, wherein the active agent is resiniferatoxin or a resiniferatoxin analogue, and wherein the patient suffers from obesity.

21. The method of any one of paragraphs 1-20, further comprising:
measuring oral glucose tolerance of the subject.

22. The method of any one of paragraphs 1-20, further comprising:
measuring body weight change in the subject.

It will be readily apparent to one of ordinary skill in the relevant arts that other suitable modifications and adaptations to the methods and applications described herein may be made without departing from the scope of the invention or any embodiment thereof. Having now described the present invention in detail, the same will be more clearly understood by reference to the following Examples, which are included herewith for purposes of illustration only and are not intended to be limiting of the invention.

EXAMPLES

Example 1

Effect of RTX on Blood Glucose Tolerance and Body Weight in Rats

Resiniferatoxin (RTX) is a naturally occurring super-analogue of capsaicin. It is found naturally in the latex of Euphorbia plants. Capsaicin (CAP) is the main pungent component in hot pepper. Resiniferatoxin and capsaicin and their analogues are exogenous ligands for the transient receptor potential cation channel subfamily V, member 1 (TRPV-1), which was formerly known as the Vanilloid receptor 1 (VR1). The only known endogenous ligand for this receptor is the proton. TRPV-1 receptors are found on the visceral sensory nerve fibers of the unmyelinated type (C-fiber) and the thinly myelinated type (A-fiber). TRPV-1 functions as a modulator of sensory nerve responses to various noxious stimuli. Prolonged exposure to capsaicin leads to the desensitization of the TRPV1 receptors and under certain situations, complete ablation of the nerves. Resiniferatoxin induces the desensitization effect and neuronal ablation more potently than capsaicin and with minimal initial activation of the TRPV-1 neuron. Resiniferatoxin, and a number of agonists based on the structures of capsaicin and resiniferatoxin have been reported as potential analgesics through desensitization/denervation of theses neurons.

Experiments with systemic capsaicin or RTX have been shown to result in improvement of type 1 and type 2 diabetes in animal model systems. See above. Without intending to be bound by theory, the effects of these agents may be due to a decrease in the release of the neurotransmitter calcitonin gene-related peptide (CGRP), which is characteristically produced by sensory nerves and released upon stimulation. CGRP can induce insulin resistance and inhibit insulin secretion in vitro. However, systemic exposure to RTX or capsaicin desensitizes sensory nerves everywhere and therefore is not desirable. The prior art is deficient in failing to localize the effects of sensory nerve desensitization to a particular organ or to a particular surface of a particular organ. As demonstrated herein, administering an active agent, such as RTX, capsaicin, or their analogues, directly to the small intestine, in particular to the duodenum, in a subject improves glucose tolerance and causes weight loss. The results provided herein thus identify for the first time a specific target for sensory nerve desensitization. The methods provided herein therefore allow for the safe treatment of diabetes and obesity by directing, for example, capsaicin or RTX to a very restricted length of the intestine, thereby reducing or eliminating systemic side effects of these agents. Further, the methods provided herein can also be used to develop new methods for the treatment of diabetes and obesity.

Methods

Animals

Adult male Sprague-Dawley rats (Harlan, Indianapolis, Ind.) weighing 280-350 g were used in all the experiments. The animal protocol was approved by the Institutional Animal Care and Use Committee of the Stanford University Medical Center.

Surgery and Resiniferatoxin (RTX) Treatment Rats were randomly divided into six groups: 1, vehicle solution treated on the surface of duodenum (n=4); 2, RTX solution treated on the surface of duodenum (n=4); 3, vehicle solution treated on the surface of ileum (1 rat) or colon (1 rat) (n=2); 4, RTX solution treated on the surface of ileum (2 rats) or colon (1 rat) (n=3); 5. Vehicle solution infuse into duodenum (n=2); 6. RTX solution infuse into duodenum (n=3).

Rats were fasted overnight prior to surgery having free access to water. Under 2% isoflurane-induced anesthesia, the abdomen was opened through a midline incision for the duodenum treatment and lower line for ileum or colon treatment. These intestines were exposed and protected with warm saline sponges around the intestine. Procedure 1: RTX application on the surface of intestine: The cotton applicator with RTX (0.32 mM) or vehicle solution were gently applied topically to the outer surface of entire duodenum (about 10 cm from the beginning of the duodenum) for 5 mM Same treatment in ileum and colon groups were applied on about 10 cm long of distal ileum and colon. Procedure 2: RTX or vehicle infused into duodenum: Two atraumatic clamps used to block on beginning and distal of duodenum. 0.8 ml of 0.32 mM RTX or vehicle was infused into duodenum through a glass syringe with a 27 gauge needle. After 30 mM the RTX or vehicle solution were withdrawn and the clamps were released. After treatment, the abdominal incisions were closed.

RTX solution: RTX stock solution: 1 mg RTX+10% ethanol+10% Tween-80 in saline to make 1 μg RTX/μl in stock solution. RTX work solution (0.32 mM): stock RTX solution (0.2 ml)+Saline (0.8 ml); Vehicle (like stock solution without RTX)

Oral Glucose Tolerance Test (OGTT)

Post RTX treatment 1st, $3^{rd}$ and $7^{th}$ week all the rats were performed the OGTT. After 17 hours overnight fasting, blood glucose was measured in conscious rats by tail-stick, using a glucose meter (Bayer Healthcare LLC, Mishawaka, Ind.). OGTT was measured before (baseline) and each 15 minutes for 2 hours after oral gavage glucose (1 g/kg body weight).

Body Weight Change Monitoring

The body weight of rats was measured before RTX treatment and each blood glucose testing day.

Data Analyses

Data are presented as means±s.e. Data were compared using Student's t-test. Differences were considered significant at <0.05.

Results

Oral Glucose Tolerance

RTX treated-rats on the surface of duodenum showed better glucose tolerance compared with vehicle group at 30 and 45-minute peak levels of post RTX treatment $1^{st}$, $3^{rd}$ and $7^{th}$ week (P<0.05 for both, FIG. 1A). RTX treated-rats on the surface of ileum or colon and RTX infusing into duodenum were not significantly different on glucose tolerance in 2 hours testing time and all of testing day compared with vehicle groups (FIGS. 1B and C).

Body Weight Change

Figure 2:
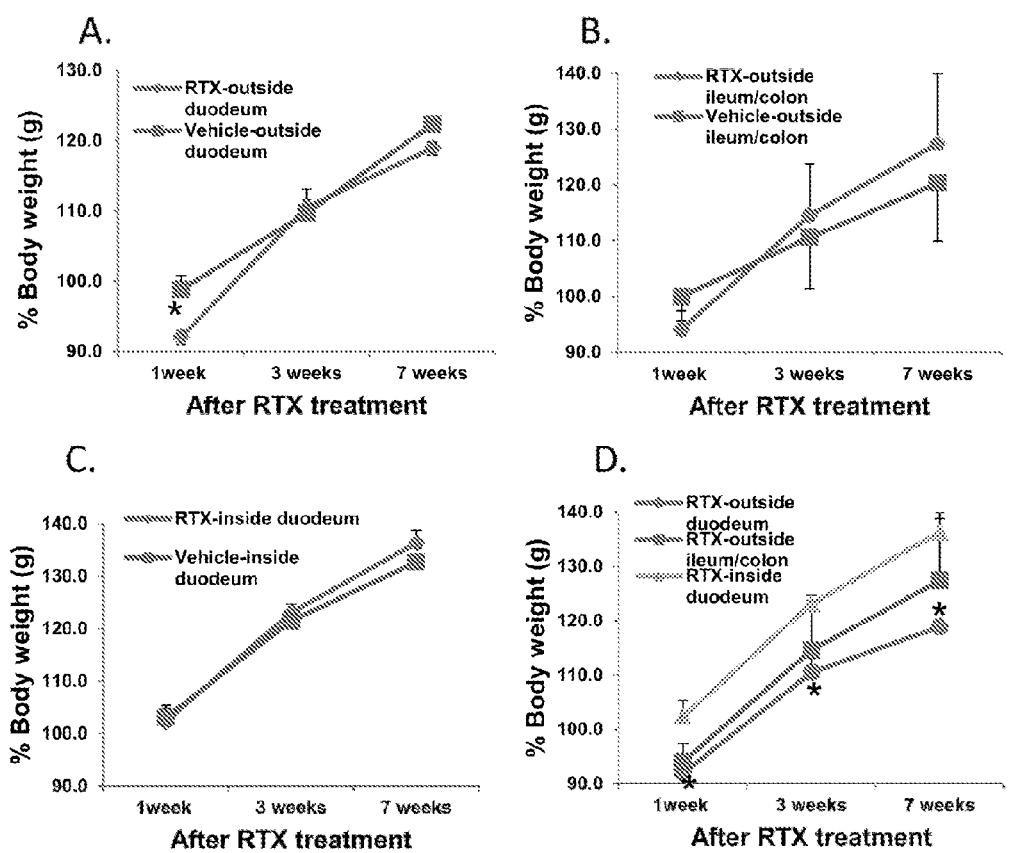
FIG. 2. Effect of RTX treatment on body weight in rats. (A) Treatment on the surface of the duodenum; (B) Treatment on the surface of the ileum/colon; (C) Infusion into the duodenum; and (D) Direct comparison of the three RTX treatments.

The body weight in rats treated on the surface of duodenum with RTX was significantly less in the $1^{st}$ week post RTX treatment compared with vehicle group (92.0±1.0 vs 98.8±2.0, P<0.05, FIG. 2A). After the $3^{rd}$ and $7^{th}$ week post RTX treatment, the body weight in both groups were not significantly different. RTX treated-rats on the surface of ileum or colon and RTX infusing into duodenum were not significantly different on body weight of all measurement day compared with vehicle groups (FIGS. 2B and C). On the other hand RTX treated-rats on the surface of duodenum shown also significantly loss of weight in $1^{st}$, $3^{rd}$ and $7^{th}$ week post RTX treatment compared with rats by RTX infusing into duodenum (92.0±1.0 vs 102.4±3.0, 110.5±2.6 vs. 123.1±1.6 and 118.9±0.9 vs. 136.3±2.5, P<0.05, FIG. 2D).

All patents, patent publications, and other published references mentioned herein are hereby incorporated by reference in their entireties as if each had been individually and specifically incorporated by reference herein.

While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined by reference to the appended claims, along with their full scope of equivalents.

What is claimed is:

1. A method of treatment comprising: targeted chemical ablation of a sensory nerve of the duodenum in a subject, wherein the targeted chemical ablation comprises administering resiniferatoxin, wherein the subject suffers from diabetes mellitus or obesity.

2. The method of claim 1, wherein the chemical ablation comprises administering the resiniferatoxin directly to a TRPV-1 receptor.

3. The method of claim 2, wherein the active agent is administered by injection.

4. The method of claim 1, wherein the active agent is administered by topical application.

5. The method of claim 2, wherein the active agent is administered by infusion through a syringe.

6. The method of claim 1, wherein the active agent is administered following surgical exposure of the small intestine of the subject.

7. The method of claim 2, wherein the active agent is administered by a laparoscope or an endoscope.

8. The method of claim 2, wherein the active agent is administered by topical application directly to the duodenum, wherein the active agent is resiniferatoxin, and wherein the patient suffers from obesity.

9. The method of claim 1, wherein the agent resiniferatoxin is administered to the sensory nerve on the serosal surface of the duodenum.

10. The method of claim 1, wherein the subject suffers from diabetes mellitus.

11. The method of claim 1, wherein the subject suffers from type 2 diabetes mellitus.

12. The method of claim 1, wherein the subject suffers from obesity.

13. The method of claims 1-12, further comprising: measuring oral glucose tolerance of the subject.

14. The method of claims 1-12, further comprising: measuring body weight change in the subject.

15. The method of claim 1, wherein the sensory nerve expresses a transient receptor potential cation channel subfamily V, member 1 (TRPV-1) receptor.

* * * * *